(12) United States Patent
Inoue et al.

(10) Patent No.: US 7,648,841 B2
(45) Date of Patent: Jan. 19, 2010

(54) REAGENT FOR DETERMINING THE ABSOLUTE CONFIGURATION OF CHIRAL COMPOUND AND DETERMINATION METHOD

(75) Inventors: Yoshihisa Inoue, Toyonaka (JP); Victor Borovkov, Toyonaka (JP); Juha Lintuluoto, Osaka (JP)

(73) Assignee: Japan Science and Technology Agency, Saitama (JP)

( * ) Notice: Subject to any disclaimer, the term of this patent is extended or adjusted under 35 U.S.C. 154(b) by 687 days.

(21) Appl. No.: 10/505,906

(22) PCT Filed: Jan. 10, 2003

(86) PCT No.: PCT/JP03/00147

§ 371 (c)(1),
(2), (4) Date: Aug. 26, 2004

(87) PCT Pub. No.: WO03/073076

PCT Pub. Date: Sep. 4, 2003

(65) Prior Publication Data

US 2005/0107604 A1    May 19, 2005

(30) Foreign Application Priority Data

Feb. 27, 2002   (JP) .............................. 2002-051505

(51) Int. Cl.
  *G01N 33/00*   (2006.01)
  *C07D 487/22*   (2006.01)
(52) U.S. Cl. .............................. 436/96; 436/73; 436/79; 436/91; 436/164; 436/166; 436/171; 436/106; 252/408.1; 540/145; 562/401

(58) Field of Classification Search ...................... 436/8, 436/73, 79, 81, 84, 91, 96, 164, 166, 171, 436/127, 106; 252/408.1; 540/145; 562/401
See application file for complete search history.

(56) References Cited

U.S. PATENT DOCUMENTS

| 5,371,122 | A  | * | 12/1994 | Kawahara et al. ............. 524/88 |
| 6,420,553 | B1 | * | 7/2002 | Inoue et al. .................. 540/145 |
| 2001/0055736 | A1 | * | 12/2001 | Sato ........................... 430/567 |
| 2003/0008406 | A1 | * | 1/2003 | Inoue et al. ................... 436/96 |
| 2006/0148091 | A1 | * | 7/2006 | Inoue et al. ................... 436/96 |

FOREIGN PATENT DOCUMENTS

| JP | 2001-220392 | * | 8/2001 |
| WO | 01/40774 | * | 6/2001 |

OTHER PUBLICATIONS

Lintuluoto et al. Journal of the American Chemical Society, vol. 124, Oct. 23, 2002, pp. 13676-13677.*

* cited by examiner

*Primary Examiner*—Maureen M Wallenhorst
(74) *Attorney, Agent, or Firm*—Knobbe Martens Olson & Bear LLP (57) ABSTRACT

The present invention relates to a reagent for determining the absolute configuration of a chiral compound containing as an active ingredient a metalloporphyrin dimer, wherein the metalloporphyrin dimer has an alkaline-earth metal ion as a central metal and has a carbon chain-crosslinked structure in which at least one of the two porphyrin rings has a substituent bulkier than methyl at least one of the second carbon atoms from a carbon atom bonded to the crosslinking carbon chain along the outer periphery of the porphyrin ring and a method for determining the absolute configuration of an asymmetric carbon atom of the chiral compound using the reagent.

16 Claims, 6 Drawing Sheets

$B_\parallel$:

Achiral

Chiral

$B_\perp$:

Achiral

Chiral

Fig. 3

Right-handed screw induced by the coordination of the (*S*)-amine

Fig. 4 a:1 in CH$_2$Cl$_2$    b:1+(R)-2-BuNH2 in CH$_2$Cl$_2$

REAGENT FOR DETERMINING THE ABSOLUTE CONFIGURATION OF CHIRAL COMPOUND AND DETERMINATION METHOD

This application is the U.S. National Phase under 35 U.S.C. §371 of International Application PCT/JP03/00147, filed Jan. 10, 2003, which claims priority of Japanese Patent Application No. 2002-51505, filed on Feb. 27, 2002. The International Application was published under PCT Article 21(2) in a language other than English.

TECHNICAL FIELD

The present invention relates to a reagent for determining the absolute configuration of chiral compounds and a method for determining the absolute configuration of chiral compounds using the reagent.

BACKGROUND OF THE INVENTION

Conventionally, the absolute configuration of chiral compounds has been determined by circular dichroism (CD) spectrophotometric measurement of a complex of a chiral compound and a specific compound based on the correlation between the sign of the Cotton effect and the absolute configuration of chiral compounds. For example, the following methods are reported.

(1) X. Huang, B. H. Rickmann, B. Borhan, N. Berova, and K. Nakanishi (J. Am. Chem. Soc., 1998, 120, 6185-6186) report that circular dichroism is induced when chiral compounds are coordinated to a long chain-crosslinked porphyrin dimer, and there is a correlation between the sign of the Cotton effect and the absolute configuration of the chiral compounds.

In this system, however, circular dichroism is induced only when one chiral compound is simultaneously coordinated to two porphyrin units. Therefore, this method is useful only for bifunctional chiral compounds such as diamines, aminoalcohols, etc.

(2) M. Takeuchi, T. Imada, and S. Shinkai (Bull. Chem. Soc. Jpn., 1998, 71, 1117-1123) report that a porphyrin dimer having a phenylboronic acid unit exhibits circular dichroism in the presence of various sugars.

This system is applicable only to sugars which bind to boronic acid, and it is not a system for directly determining the absolute configuration of any specific-asymmetric center among the many asymmetric centers of sugars.

As is clear from the above, there have been no reports of a method for determining the absolute configuration applicable to a wide variety of chiral compounds, such as monoalcohols, etc.

X-ray diffraction is a known method for determining the absolute configuration of chiral compounds. However, the compounds to which this method is applicable are limited to crystalline compounds.

The present inventors have investigated methods for precisely and easily determining the absolute configuration of various chiral compounds. In recent years, they have found that circular dichroism is induced when a chiral compound is coordinated to a metalloporphyrin dimer containing Zn, Fe, Mn, or Ru as the central metals, and the sign of the Cotton effect and the absolute configuration of the chiral compound are correlated with each other. A novel method for determining the absolute configuration of chiral compounds was thus completed based on this finding (Japanese Unexamined Patent Publication No. 2001-220392).

However, even this method arises a problem such that the induced Cotton effect cannot be detected in the case of a chiral compound of a monoalcohol, etc. unless the sample solution is cooled to about −80° C.

DISCLOSURE OF THE INVENTION

The present invention is made in view of the problems of the prior art, and the principal object is to provide a reagent which allows the easy (i.e., without the complicated operation of cooling, etc.), highly-sensitive and precise determination of the absolute configuration of chiral compounds such as monoalcohols, etc., and a method for determining the absolute configuration of chiral compounds using the reagent.

The present inventors conducted intensive research and found that the objects can be attained by a reagent containing a specific metalloporphyrin dimer as an active ingredient, and a method using the reagent, to thereby accomplish the present invention.

More specifically, the present invention relates to a reagent for determining the absolute configuration of chiral compounds and a determination method thereof as described below.

1. A reagent for determining the absolute configuration of a chiral compound containing as an active ingredient a metalloporphyrin dimer, wherein the metalloporphyrin dimer has an alkaline-earth metal ion as a central metal and has a carbon chain-crosslinked structure in which at least one of the two porphyrin rings has a substituent bulkier than methyl at at least one of the second carbon atoms from a carbon atom bonded to the crosslinking carbon chain along the outer periphery of the porphyrin ring.

2. A reagent for determining the absolute configuration of a chiral compound according to Item 1, wherein the carbon chain-crosslinked metalloporphyrin dimer is a metalloporphyrin represented by formula (1):

Formula (1)

wherein $M^{2+}$ and $M'^{2+}$ are the same or different and each represent an alkaline-earth metal ion, n is 2 or 3, $R^a$ to $R^d$ are the same or different and each represent a hydrogen atom or a substituent bulkier than methyl, at least one of $R^a$ to $R^d$ represents a substituent bulkier than methyl, and $R^1$ to $R^{12}$ are the same or different and each represent a hydrogen atom or a hydrocarbon group.

3. A reagent according to Item 2, wherein at least one of $R^a$ to $R^d$ in formula (1) is one member selected from the group consisting of 1) a $C_1$-$C_8$-hydrocarbon group, 2) an oxygen-containing substituent, 3) a nitrogen-containing substituent, 4) a halogen atom, and 5) a halogenated hydrocarbon group.

4. A method for determining the absolute configuration of a chiral compound comprising analyzing a sample solution containing a reagent according to Item 1 and the chiral compound by circular dichroism spectrophotometry to determine the absolute configuration of an asymmetric carbon of the chiral compound based on a sign of the Cotton effect, the chiral compound having the following characteristics:

(i) being capable of coordinating to the metalloporphyrin dimer as an active ingredient, and

(ii) having a group capable of coordinating to the metalloporphyrin dimer directly bonded to the asymmetric carbon atom, or having one carbon atom separating the group capable of coordinating to the metalloporphyrin dimer and the asymmetric carbon atom.

5. A method according to Item 4, wherein the chiral compound is selected from one member of the group consisting of 1) a primary monoamine, 2) a secondary monoamine, 3) a monoalcohol, and 4) an aminoalcohol.

6. A method according to Item 4, wherein the circular dichroism spectrophotometric measurement is conducted at −10° C. to 30° C.

The present invention relates to a reagent for determining the absolute configuration of chiral compounds comprising as an active ingredient a metalloporphyrin dimer which has alkaline-earth metal ion as the central metal and which has a carbon chain-crosslinked metalloporphyrin dimer structure in which at least one of the two porphyrin rings has a substituent bulkier than methyl at at least one of the second carbon atoms from the carbon atom bonded to the crosslinking carbon chain along the outer periphery of the porphyrin ring.

The metalloporphyrin dimer contained as an active ingredient is not limited as long as it satisfies the above-described conditions, and includes compounds represented by formula (1):

Formula (1)

In formula (1), $M^{2+}$ and $M'^{2+}$ represent a central metal. $M^{2+}$ and $M'^{2+}$ may be the same or different and each represent an alkaline-earth metal ion such as $Mg^{2+}$, $Ca^{2+}$, $Sr^{2+}$, and $Ba^{2+}$. Among these, $Mg^{2+}$ and $Ca^+$ are preferable, and $Mg^{2+}$ is particularly preferable.

The metalloporphyrin dimer used in the invention has a structure such that two metalloporphyrin units are cross-linked by a carbon chain. For example, in the compound represented by formula (1), the two metalloporphyrin units are cross-linked by $-(CH_2)_n-$. The number of carbon atoms in the crosslinking carbon chain is not limited and is generally about 2 or 3, and preferably 2. In formula (1), for example, n is 2 or 3, and preferably 2.

In formula (1), each $R^a$ to $R^d$ is a substituent bonded to second carbon atoms from the carbon atom bonded to the cross-linking carbon chain along the outer periphery of the porphyrin ring. In the metalloporphyrin dimer used in the invention, at least one of the second carbon atoms of the porphyrin rings from the carbon atom bonded to the crosslinking carbon chain along the outer periphery of the porphyrin ring is substituted with a substituent bulkier than methyl.

In formula (1), $R^a$ to $R^d$ is the same or different and each represent a hydrogen atom or a substituent bulkier than methyl so long as at least one of $R^a$ to $R^d$ represents a substituent bulkier than methyl.

A substituent bulkier than methyl means a substituent whose volume is as large as or larger than a methyl group. Examples of such substituents include 1) $C_{1-8}$ hydrocarbon groups, 2) oxygen-containing substituents, 3) nitrogen-containing substituents, 4) halogen atoms, and 5) halogenated hydrocarbon groups, etc.

Examples of 1) $C_{1-8}$ hydrocarbon groups include linear or branched alkyl group such as methyl, ethyl, propyl, n-butyl, isobutyl and the like. The number of carbon atoms of the hydrocarbon group is preferably 1 to about 4.

Examples of 2) oxygen-containing substituents include esters, carboxylalkyls, etc. Examples of esters include methyl esters, ethyl esters, etc. Examples of carboxylalkyls include carboxymethyl, etc.

Examples of 3) nitrogen-containing substituents include aminos, amides, 2-aminoethyl, etc.

Examples of 4) halogen atoms include Cl, Br, F, etc.

Examples of 5) halogenated hydrocarbon groups include chloromethyl, chloroethyl, chloropropyl, chlorobutyl, etc.

In formula (1), $R^1$ to $R^{12}$ are the same or different and each represent a hydrogen atom, a hydrocarbon group, etc. Examples of hydrocarbon groups include a linear or branched alkyl groups such as methyl, ethyl, propyl, n-butyl, isobutyl, etc. The number of carbon atoms in the hydrocarbon groups represented by $R^1$ to $R^{12}$ is not limited and is generally 1 to about 10, and preferably 1 to about 4.

A compound represented by formula (2) can be preferably used as the metalloporphyrin dimer used in the invention. Hereinafter, the compound represented by formula (2) is sometimes referred to as "Compound 1."

Formula (2)

The reagent of the invention may contain additional ingredients within ranges in which the desired effect of the invention can be attained.

The method for producing the metalloporphyrin dimer to be used in the present invention is not limited, and the metalloporphyrin dimer can be synthesized according to known methods. For example, the metalloporphyrin dimer can be produced by a method for introducing alkaline-earth metal ions as central metals into unmetalated porphyrin dimer) (which, hereinafter, is sometimes referred to as "a free base porphyrin dimer") by reacting the free base porphyrin dimer with an alkaline-earth metal halide (for example, $MgBr_2 \cdot Et_2O$, etc.) in the presence of basic compounds such as triethylamine, pyridine, methylpyridine, dimethylpyridine, diazine, methyldiazine, pyrazine, ethylpyrazine, pyrimidine, piperazine, morpholine, etc.

The free base porphyrin dimer can be produced by known methods. For example, the method proposed by V. V. Borovkov, J. M. Lintuluoto and Y. Inoue (Helv. Chem. Acta., 1999, 82, 919-934); and V. V. Borovkov, J. M. Lintuluoto and Y. Inoue (Synlett., 1998, 768), etc., can be mentioned.

An alkaline-earth metal ion can also be introduced to the free base porphyrin dimer by a known method such as a method proposed by, for example, J. S. Lindsey and J. N. Woodford (Inorg. Chem. 1995, 34, 1063-1069).

The absolute configuration of an asymmetric carbon atom of a chiral compound can be determined from the sign of the Cotton effect revealed by the analysis of circular dichroism spectrophotometry of the reagent of the invention and the chiral compound. The chiral compound has the following characteristics (1) and (2).

(1) a chiral compound which can be coordinated to the metalloporphyrin dimer as an active ingredient, and (2) a chiral compound in which the group capable of coordinating to the metalloporphyrin dimer and asymmetric carbon are directly bonded to each other or a chiral compound in which one carbon atom separates the group that can be coordinated to the metalloporphyrin dimer and the asymmetric carbon.

The present invention includes a method for determining the absolute configuration of the asymmetric carbon atom of a chiral compound based on the sign of the Cotton effect revealed by the analysis of circular dichroism spectrophotometry of a sample solution containing the above-mentioned reagent and the chiral compound. The chiral compound has the following characteristics (1) and (2).

(1) the chiral compound which can be coordinated to the metalloporphyrin dimer as an active ingredient; and (2) the chiral compound in which the group that can be coordinated to the metalloporphyrin dimer and the asymmetric carbon atom are directly bonded to each other, or the chiral compound in which one carbon atom separates the group that can be coordinated to the metalloporphyrin dimer and the asymmetric carbon atom.

Examples of compounds that can be coordinated to the metalloporphyrin dimer include compounds containing basic groups such as an amino group, a hydroxyl group, etc. as a group capable of coordinating to the metalloporphyrin dimer. More specifically, 1) primary monoamines, 2) secondary monoamines, 3) monoalcohols, 4) aminoalcohols, etc. In the case of an aminoalcohol, the amino group readily coordinates to the metalloporphyrin dimer, thus determining the absolute configuration of an asymmetric carbon atom directly bonded to the amino group or an asymmetric carbon atom separated by one carbon atom from the amino group.

The method of the present invention can determine the absolute configuration of a chiral compound in which the group that can be coordinated to a central metal of the metalloporphyrin dimer as an active ingredient and the asymmetric carbon atom are bonded to each other, or a chiral compound in which one carbon atom separates the group that can be coordinated to a central metal of the metalloporphyrin dimer and the asymmetric carbon atom. For example, 2-butanol, 1-phenylethanol, 1-phenylethylamine, etc. are equivalent to the chiral compounds in which the group that can be coordinated to a central metal of the metalloporphyrin dimer and the asymmetric carbon atom are directly bonded to each other. 2-methyl-1-butylamine, etc. can be mentioned as an example of a chiral compound in which one carbon atom is present between the group that can be coordinated to a central metal of the metalloporphyrin dimer and the asymmetric carbon atom.

In the case of a chiral compound having two or more asymmetric carbon atoms, such as borneol, menthol, etc., the absolute configuration of an asymmetric carbon atom directly bonded to the group that can be coordinated to a central metal of the porphyrin dimer, or an asymmetric carbon atom that is separated by one carbon atom from the group that can be coordinated to the porphyrin dimer can be determined.

The sample solution used for the circular dichroism spectrophotometric measurement contains the above-mentioned reagent and a chiral compound. Methods for preparing the sample solution are not limited, and the solution can be prepared, for example, by a method of dissolving into a solvent the metalloporphyrin dimer as an active ingredient, the chiral compound, etc.

A solvent which does not coordinate to the metalloporphyrin dimmer is preferred for use in preparing the sample solution. Examples of such solvents include halogenated aliphatic hydrocarbons such as chloroform ($CHCl_3$), dichloromethane ($CH_2Cl_2$), dichloroethane ($CH_2ClCH_2Cl$), tetrachloroethane ($CHCl_2CHCl_2$), carbon tetrachloride ($CCl_4$), etc., and aliphatic hydrocarbons such as hexane, heptane, etc.

The concentrations of the chiral compound and metalloporphyrin dimer in the sample solution are not limited. The lower concentration limit is not limited as long as the first or second Cotton effect is detectable, and can be suitably determined depending on the type of metalloporphyrin dimer, chiral compound, solvent, etc. to be used. The upper concentration limit of the chiral compound and the metalloporphyrin dimer in the sample solution are determined so that the ellipticity value of the first or second Cotton effect in the circular dichroism spectra (CD spectra) is, for example, about at least twice the noise level (for example, about 1 mdeg or more). Preferably, the ellipticity value of the first or second Cotton effect is the greatest possible within the voltage range of a photomultiplier tube of up to −700 kV. More preferably, the ellipticity of the first or second Cotton effect is about 10 mdeg to about 50 mdeg.

The concentration of the chiral compound in the sample solution can be suitably determined depending on type of chiral compound, etc. and is generally about $10^{-4}$ mol/l or more, preferably about $10^{-5}$ mol/l to about $10^{-1}$ mol/l, and more preferably about $10^{-4}$ mol/l to about $10^{-3}$ mol/l.

The concentration of the metalloporphyrin dimer in the sample solution can be suitably determined depending on type of chiral compound, etc. and is generally about $10^{-7}$ mol/l or more, and preferably about $10^{-6}$ mol/l or more. The upper limit of the concentration of the metalloporphyrin dimer in the sample solution can be suitably determined without limitation depending on type of chiral compound, etc. and is generally about $5 \times 10^{-5}$ mol/l or less, and preferably about $5 \times 10^{-6}$ mol/l or less.

The lowest concentrations of chiral compound in the sample solution required for effectively detecting the Cotton effect are as follows. When Compound I represented by the above-mentioned formula (2) is used as a reagent, an acyclic primary monoamine is about $10^{-6}$ mol/l, a cyclic aromatic monoamine is about $10^{-5}$ mol/l, a secondary monoamine is about $10^{-6}$ mol/l, an aminoalcohol is about $10^{-4}$ mol/l and a monoalcohol is about $10^{-1}$ to about $10^{-2}$ mol/l. Even when a monoalcohol is used, the Cotton effect can be effectively detected by use of a metalloporphyrin dimer of the above-mentioned concentration at about −10° C. to about 30° C.

The temperature for the circular dichroism spectrophotometric measurement is not limited as long as the Cotton effect is detectable. High-sensitivity measurements can be conducted at low temperatures, but the Cotton effect can be detected even when the sample solution is not cooled.

The following cases 1 to 4 can be mentioned as examples showing more specific analysis conditions.

<Case 1> Determination of the Absolute Configuration of Primary Monoamines:

Chloroform, dichloromethane, carbon tetrachloride, tetrachloroethane, hexane, heptane, dichloroethane, etc. are preferred as solvents. The concentration of an acyclic primary monoamine in the sample solution is preferably $10^{-6}$ mol/l or more, and the concentration of a cyclic aromatic monoamine is preferably about $10^{-5}$ mol/l or more. When the magnesium porphyrin dimer represented by the above-mentioned formula (2) is used, its concentration in the sample solution is preferably about $10^{-6}$ mol/l or more. Examples of primary monoamines as a measurement target include 2-butylamine, 1-phenylethylamine, 1-(1-naphthyl)ethylamine, 1-cyclohexylethylamine, 2-methyl-1-butylamine, [endo-(1R)-1,7,7-trimethylbicyclo[2,2,1]heptane-2-amine], etc.

<Case 2> Determination of the Absolute Configuration of Secondary Monoamines:

Chloroform, dichloromethane, carbon tetrachroide, tetrachloroethane, hexane, heptane, dichloroethane, etc. are preferable as solvents. The concentration of secondary monoamine in the sample solution is preferably about $10^{-6}$ mol/l or more. When the magnesium porphyrin dimer (Compound 1) represented by the above-mentioned formula (2) is used, the concentration thereof in the sample solution is preferably about $10^{-6}$ mol/l or more. Examples of secondary monoamines as a measurement target include N-methyl-1-phenylethylamine, etc.

<Case 3> Determination of the Absolute Configuration of Aminoalcohols:

Examples of preferable solvents include chloroform, dichloromethane, carbon tetrachloride, tetrachloroethane, hexane, heptane, dichlorioethane, etc. The concentration of aminoalcohol in the sample solution is preferably about $10^{-4}$ mol/l or more. When Compound 1 is used, the concentration thereof in the sample solution is preferably about $10^{-6}$ mol/l or more. Examples of aminoalcohols as a measurement target include 1-amino-2-propanol, 2-amino-4-methyl-1-pentanol, etc.

<Case 4> Determination of the Absolute Configuration of Monoalcohols:

Methane dichloride or hexane is preferred as a solvent. The concentration of monoalcohol in the sample solution is preferably about $10^{-2}$ mol/l or more. When Compound 1 represented by the above-mentioned formula (2) is used, the concentration thereof in the sample solution is preferably about $10^{-6}$ mol/l or more. Measurement temperature is usually set from $-10°$ C. to $30°$ C., but the Cotton effect can be detected at the temperature within the range when the sample solution is not cooled. Borneol, 2-butanol, 1-phenylethanol, etc. are examples of monoalcohol as measurement targets.

The circular dichroism spectra of sample solutions show two peaks (one maximum value and one minimum value). Hereinafter, the peak occurring at longer wavelength is sometimes referred to as the "first Cotton effect", whereas the peak occurring at shorter wavelength is sometimes referred to as the "second Cotton effect". The signs of the peaks may be positive or negative. The sign of the first Cotton effect and the sign of the second Cotton effect are different from each other.

Figure 5:
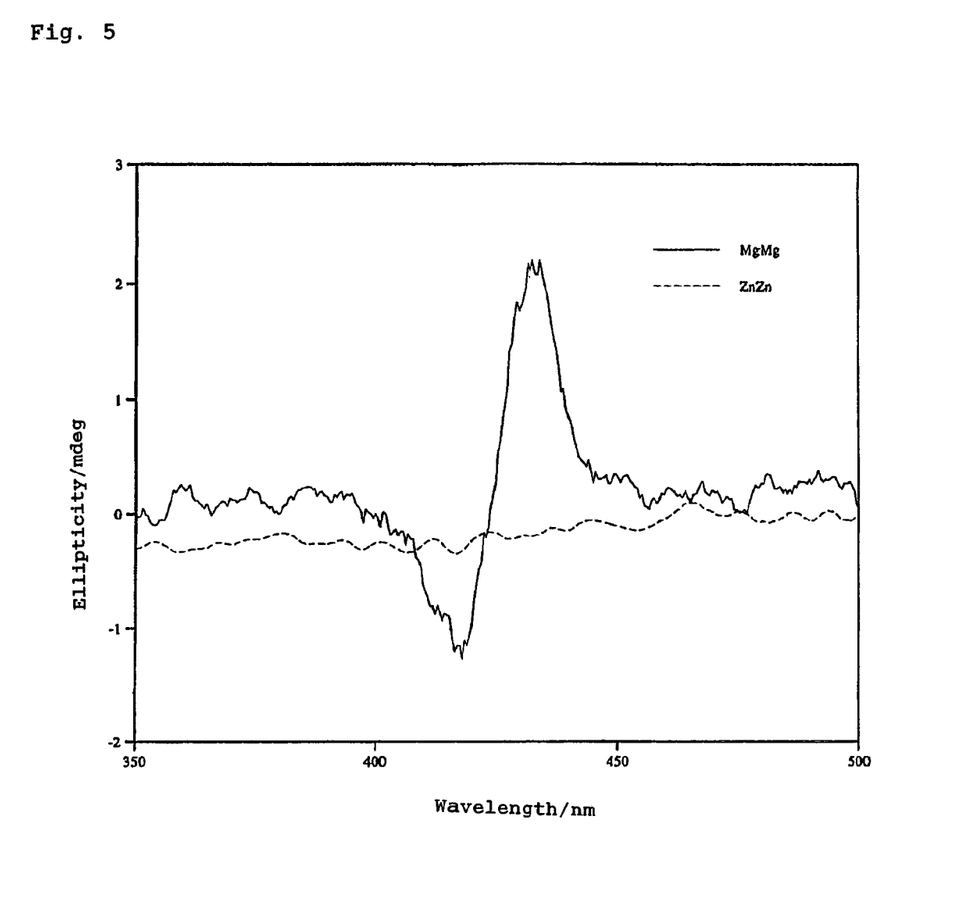
FIG. 5 shows CD spectra of a sample solution containing (S)-(−)-1-phenylethanol measured in Example 2 (shown by the solid line) and a sample solution containing (S)-(−)-1-phenylethanol measured in Comparative Example 1 (shown by the dotted line).

When the CD spectra of (S)-(-)-1-phenylethanol shown in FIG. 5 are taken as an example, the sign of the first Cotton effect is positive (plus) and the sign of the second Cotton effect is negative (minus). The signs of the Cotton effects of each optical isomer (for example, R isomer and S isomer) are reversed. For example, in the case of (S)-(+)-1-phenylethanol, the signs of the Cotton effect are reversed from the signs in the case shown in FIG. 1, and more specifically, the sign of the first Cotton effect is negative and the sign of the second Cotton effect is positive. The sign of either peak may be used for the determination of the absolute configuration; the first Cotton effect is usually more easily detected and thus is more preferably used.

In order to clarify a certain correspondence between the sign of each Cotton effect and the absolute configuration (R isomer or S isomer) of the asymmetric carbon atom of the chiral compound in the sample solution, CD spectra of sample solutions each containing the reagent of this invention and one of various chiral compounds whose absolute configuration is known were measured. The Table 1 shows the absolute configuration and sign of various chiral compounds, and the sign of each Cotton effect in the sample solution. The metalloporphyrin containing Mg as a central metal (Compound 1) represented by the above-mentioned formula (2) is used as the metalloporphyrin dimer, and the concentration in the sample solution was adjusted to $10^{-6}$ mol/l. The concentration of each chiral compound in the sample solution was adjusted to $10^{-4}$ mol/l when using amine and aminoalcohol, and was adjusted to $10^{-2}$ mol/l when using alcohol.

TABLE 1

| Chiral Compound | Absolute configuration and sign of a chiral compound | Sign of second Cotton effect ($B_\perp$ transition) | Sign of first Cotton effect ($B_\parallel$ transition) |
| --- | --- | --- | --- |
| 2-Butanol | (R)-(-) | + | - |
| 1-Phenylethanol | (S)-(-) | - | + |
| Borneol | (1S, 2R)-(-) | + | - |
| Menthol | (1S, 2R, 5S)-(+) | - | + |
|  | (1R, 2S, 5R)-(-) | + | - |
| 1-Naphthylethanol | (R)-(+) | + | - |
| Trans-2-phenylcyclohexanol | (1S, 2R) | - | + |
| Cis-verbenol | (1S) | - | + |
| Diacetone-D-glucose | (3S) | - | + |
| 2-Butylamine | (R)-(-) | + | - |
| 1-Phenylethylamine | (R)-(+) | + | - |
| 2-Methyl-1-butylamine | (S)-(-) | - | + |
| 1-Amino-2-propanol | (S) | - | + |

As is evident from Table 1, there is a certain correspondence between the sign of each Cotton effect and the steric configuration of the asymmetric carbon atom at the α or β position of the amino group or hydroxy group. More specifically, a positive sign of the first Cotton effect corresponds to an (S) absolute configuration at the asymmetric carbon at the above-mentioned α or β position. In contrast, a negative sign of the first Cotton effect corresponds to an (R) absolute configuration at the asymmetric carbon at the above-mentioned α or β position. From this correlation and the sign of the Cotton effect of a sample solution whose absolute configuration is unknown can be determined, the absolute configuration of a chiral compound in such solution.

Figure 2:
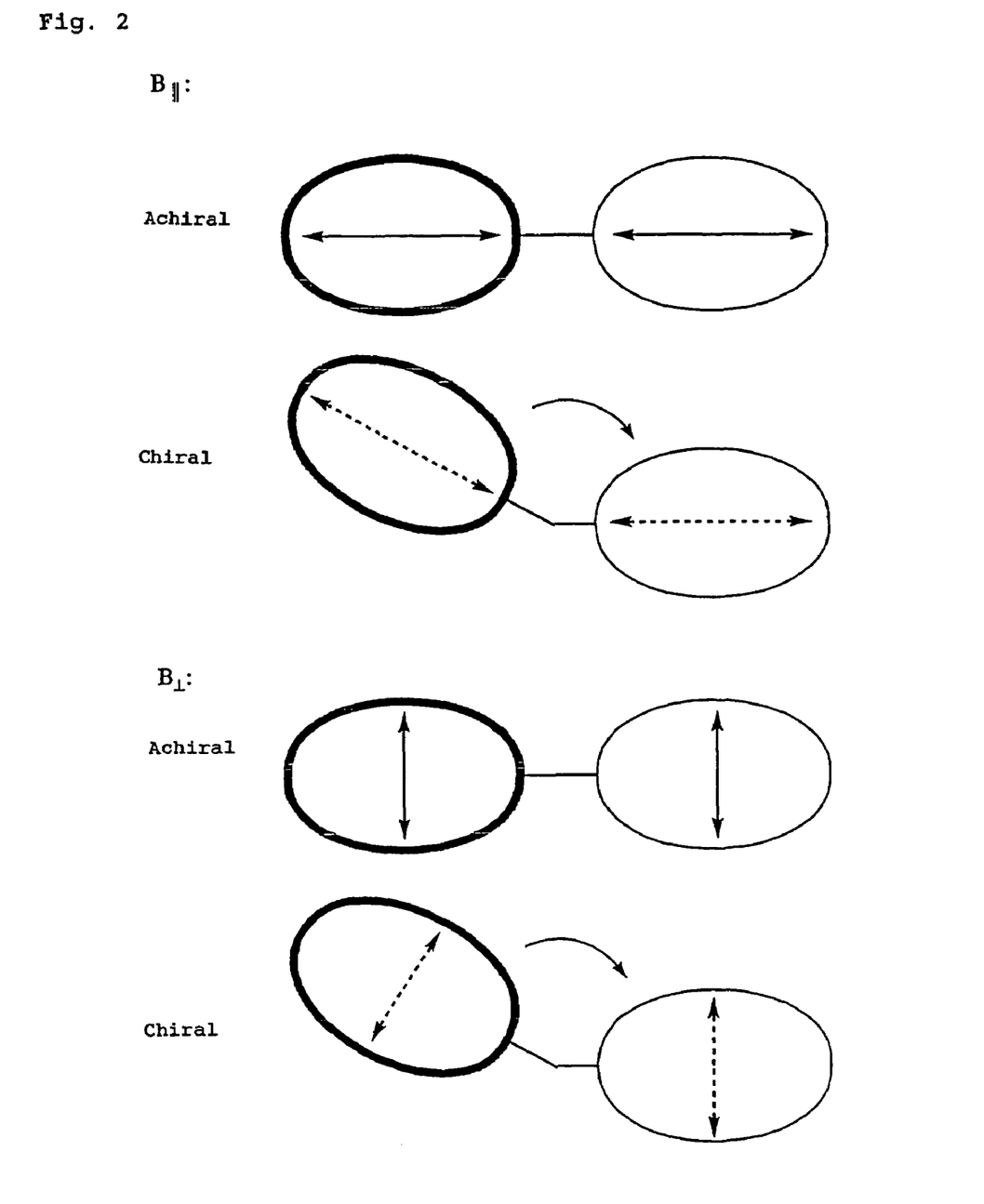
FIG. 2 schematically illustrates the dipole moment directions of the B band as the maximum absorption band of a porphyrin dimer, in which a metalloporphyrin dimer is schematically illustrated with an ellipse depicting each porphyrin ring and a straight or kinked line depicting the crosslinking carbon chain. The two ellipses (porphyrin rings) do not exist in the same plane but are located in front and rear. In order to clarify the relative positions of the two ellipses, the front ellipse is shown thickened. The chiral structure has a clockwise chirality.

In Table 1, the $B_\parallel$ transition occurs when the moments (transition moments) of two porphyrin rings are aligned in the direction of bonding the porphyrin rings and the resulting absorption band is termed the B-band (or Soret band). The $B_\perp$ transition is a transition occurring when the moments of two porphyrin rings are in directions perpendicular to the direction of bonding the porphyrin rings and the resulting absorption band is also the B-band. In FIG. 2, the direction of the moments of an "achiral" metalloporphyrin dimer to which a chiral compound is not coordinated is shown by solid double-headed arrows.

In contrast, in either the $B_\parallel$ transition or the $B_\perp$ transition, the directions of the moments of the two porphyrin rings of a chiral metalloporphyrin dimer to which a chiral compound is coordinated are slightly misaligned with respect to each other, as compared to the achiral porphyrin dimer, as shown by the dotted double-headed arrows in FIG. 2.

Figure 1:
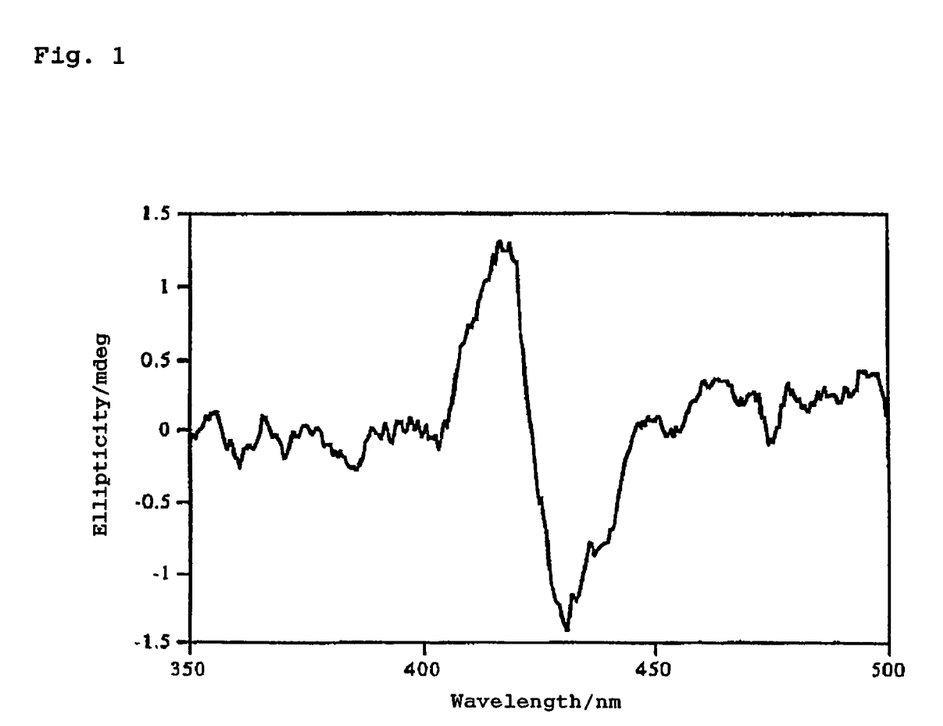
FIG. 1 shows the result obtained in Example 1 and shows CD spectra of a sample solution containing borneol.

Hereinafter, the mechanism of the induced Cotton effect in the present invention is described. A chiral compound is coordinated to a central metal of the metalloporphyrin dimer in a solution containing the metalloporphyrin dimer as an active ingredient and the above-mentioned chiral compound. The chiral compound may be coordinated to either one of the two central metals. For example, when either one of the two porphyrin rings has at least one substituent bulkier than methyl, the chiral compound is coordinated to the central metal of the other porphyrin ring instead of the porphyrin ring having such a substituent. More specifically, the chiral compound is coordinated to $M'^{2+}$ when only $R^a$ of the compound represented by the above-mentioned formula (1) is a substituent bulkier than methyl. The metalloporphyrin dimer shows a conformational change from syn to anti with such orientation of a chiral compound, and at the same time, asymmetry is induced in the anti conformer, whereby circular dichroism is exhibited as shown in FIG. 1. The syn conformer of Compound 1 represented by the above-mentioned formula (2) is shown below.

Figure 3:
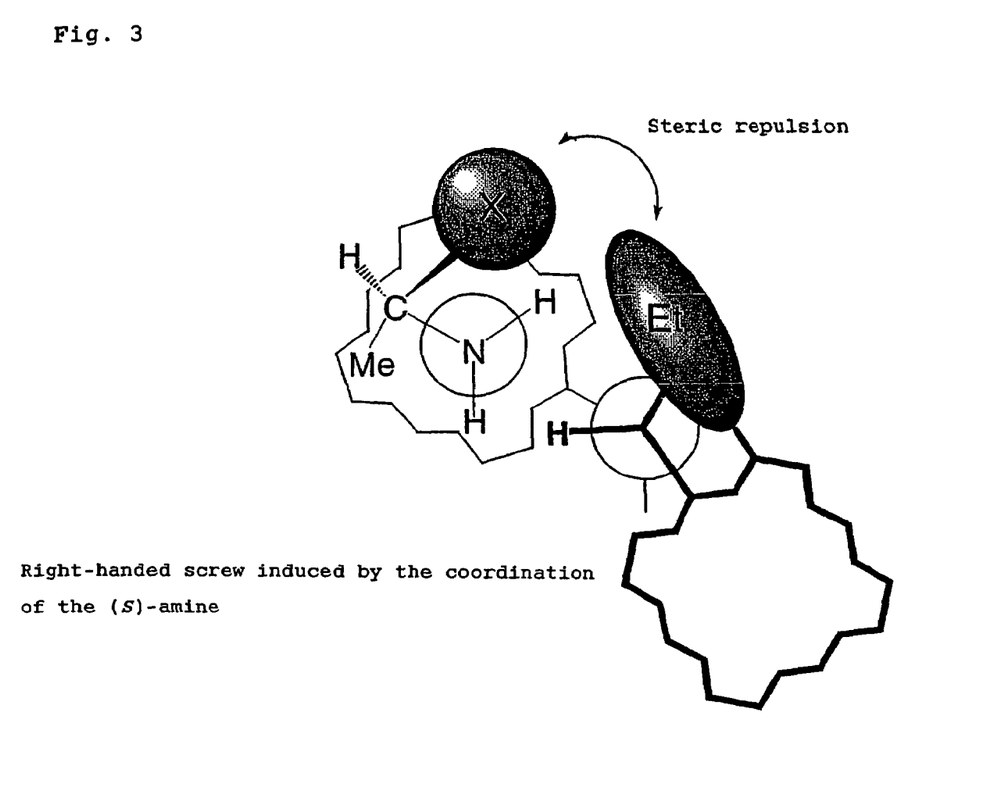
FIG. 3 schematically illustrates a mechanism of asymmetry induction in a magnesium porphyrin dimer, in which the front porphyrin ring of the two porphyrin rings is shown thickened.

The mechanism of the asymmetry induction is illustrated in FIG. 3 which shows the porphyrin rings are twisted. FIG. 3 illustrates the case where an S-amine is used as the chiral compound. Thus it can be understood that the porphyrins' orientation is twisted by the steric hindrance between the bulkiest substituent (X) bonded to the α or β carbon atom (α carbon atom in FIG. 3) of the chiral compound as a ligand and the substituent bulkier than a methyl group (Et: ethyl in FIG. 3) of the porphyrin ring to which the chiral compound is not coordinated, thereby producing circular dichroism based on the exciton interaction between the porphyrins.

According to the CD exciton-chirality method (Harada, N., Nakanishi, K., "Circular Dichroic Spectroscopy-Exciton Coupling in Organic Stereochemistry, University Science Books, Mill Valley, 1983; Nakanishi, K., Berova, N., "In Circular Dichroism; Principles and Applications", Woody, R., Ed, VCH Publishers; New York, 1994; pp. 361-398), a clockwise orientation when viewed from the front of two interacting electronic transition moments produces positive chirality, while a counterclockwise orientation leads to negative chirality.

For example, when a chiral compound of (S) absolute configuration is coordinated to the metalloporphyrin dimer, the porphyrin is clockwise twisted when viewed from the front (see FIG. 3), and thus the sign of the first Cotton effect is "positive". In contrast, when a chiral compound of (R) absolute configuration is coordinated to the metalloporphyrin dimer, the porphyrin is counterclockwise twisted when viewed from the front, and thus the sign of the first Cotton effect is "negative".

The method of the invention is used for circular dichroism (CD) spectrophotometric measurement of a sample solution containing a chiral compound, a metalloporphyrin, etc. More specifically, according to the method of the invention, the absolute configuration of chiral compounds can be determined by the sign of the Cotton effect of the circular dichroism spectra obtained when a chiral compound as a measurement target is coordinated to the metalloporphyrin dimer. According to this method, the absolute configuration of chiral compounds can be directly observed without the introduction of any specifically modified group.

BEST MODE FOR CARRYING OUT THE INVENTION

Hereinafter, the present invention will be described in detail with reference to Examples, but is not limited thereto.

A JASCO J-720WI spectropolarimeter was used to measure CD spectra.

PRODUCTION EXAMPLE 1

Figure 4:
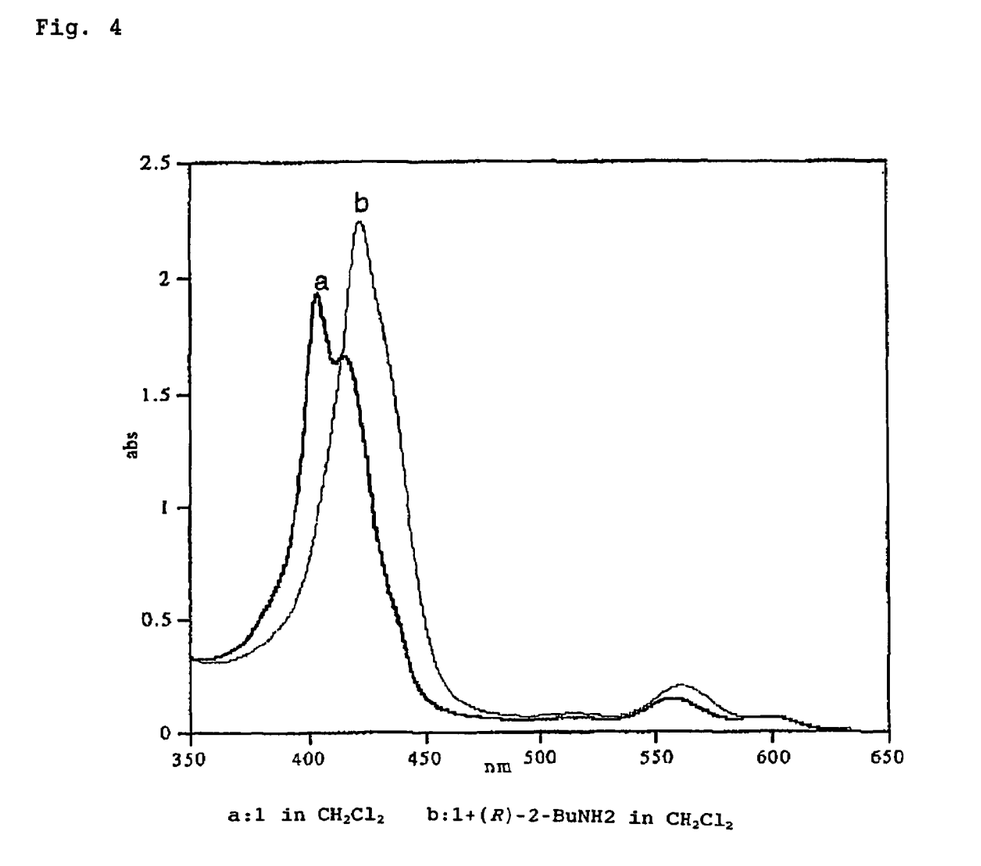
FIG. 4 shows UV-visible absorption spectra of Compound 1 prepared in Production Example 1 (shown by the thick line "a"). (R)-2-butylamine was added to a solution of Compound 1, which changes the spectra (shown by the thin line "b"). This shows that there is a certain interaction between Compound 1 and (R)-2-butylamine.

A magnesium porphyrin dimer was produced according to the following scheme.

line "a"). Absorption maxima: $\lambda_{max}$ was as follows: $\lambda_{max}$/nm: 601 (3.83), 557 (4.18), 416 (5.22), 404 (5.29). The values in brackets show the logarithm of the molar absorption coefficient for each maximum absorption: $\log_\epsilon$.

FIG. 4 also shows UV-visible absorption spectra of the solution obtained by further adding (R)-2-butylamine to the $CH_2Cl_2$ solution of Compound 1 (shown by the thin line "b").

Example 1

A $CH_2Cl_2$ solution containing about $10^{-6}$ mol/l of Compound 1 and about $10^{-1}$ mol/l of (1S, 2R)-(−)-borneol was prepared in a 3 ml cell (optical path length: 1 cm), and circular dichroism spectra were observed over the region from 350 to 500 nm at 22 to 23° C. FIG. 1 shows the result.

A free base porphyrin dimer (Compound 2, 1.9 mg, 1.73 μmol) was dissolved in anhydrous $CH_2Cl_2$ (1 ml); triethylamine (9.5 μl, 68 μmol) was further added thereto, and $(CH_2H_5)_2O\cdot MgBr_2$ (10 mg, 35 μmol) was further added. The obtained mixture was stirred at room temperature for one hour. 10 ml of $CH_2Cl_2$ was added to this mixture to dilute it and the reaction mixture was washed with 5 ml of water, dried with anhydrous sodium sulfate and filtered. The obtained filtrate was concentrated to 1 ml. A column charged with basic activated alumina (manufacture by Merck, active aluminium oxide 90) was used for column chromatographic purification. $CH_2Cl_2$ was used as a first eluate (unreacted free-base was not detected), and a mixed solvent with 1:1 ratio of $CH_2Cl_2$ to acetone was used as a second eluate. 1.95 mg of Compound 1 (98% yield with respect to free base porphyrin dimer Compound 2) was obtained by drying the second eluate by evaporation. UV-visible absorption spectra in $CH_2Cl_2$ of the obtained compound are shown in FIG. 4 (shown by the thick As is evident from FIG. 1, from the negative sign of the First Cotton effect at longer wavelengths, the (R) absolute configuration of the asymmetric carbon atom bonded to the hydroxyl group of borneol was confirmed.

Example 2

Circular dichroism spectra were measured in the same manner as in Example 1 except that $10^{-2}$ mol/l of (S)-(−)-1-phenylethanol was used instead of borneol. FIG. 5 (solid line) shows the results.

In this case, from the positive sign of the first Cotton effect, the (S) absolute configuration was confirmed.

Example 3

Figure 6:
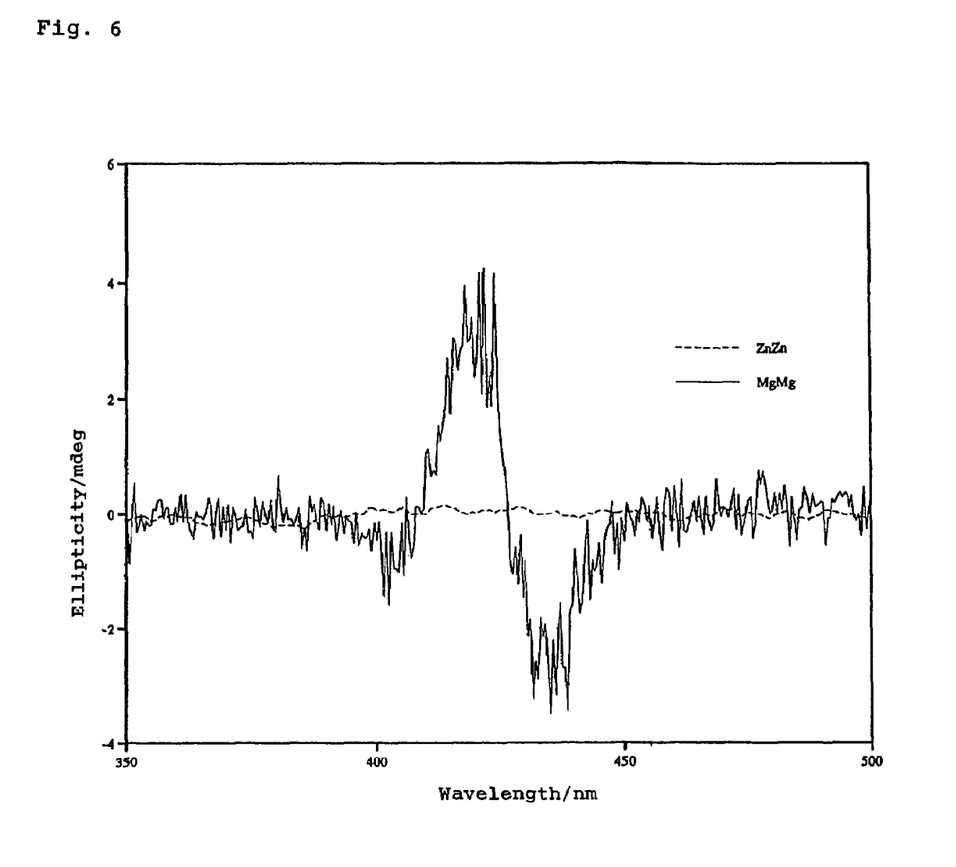
FIG. 6 shows CD spectra (shown by the solid line) of a sample solution containing (S)-(−)-1-phenylethylamine measured in Example 2 and shows CD spectra (shown by the dotted line) of a sample solution containing (S)-(−)-1-phenyl-ethylamine measured in Comparative Example 1.

Circular dichroism spectra were measured in the same manner as in Example 1 except that $10^{-4}$ mol/l of phenylethylamine was used instead of borneol. FIG. 6 (solid line) shows the result. In this case, from the negative sign of the first Cotton effect, the (R) absolute configuration was confirmed.

Comparative Example 1

Circular dichroism spectra of a sample solution containing 1-phenylethanol were measured in the same manner as in Example 2 except that a zinc porphyrin dimer (approximately $10^{-6}$ mol/l) represented by formula below was used instead of Compound 1 as a reagent to determine the absolute configuration of a chiral compound.

FIG. 5 (dotted line) shows the results. The absolute configuration of 1-phenylethanol was not determined since the Cotton effect was not detected. However, the Cotton effect was detected when the sample solution was cooled to about $-80°$ C.

{μ-{{5,5'-(ethane-1,2-diyl)bis[2,3,7,8,12,13,17,18-octaethyl-21H,23H-porphyrinato](4-)}-$_κ$N$^{21}$, $_κ$N$^{22}$, $_κ$N$^{23}$, $_κ$N$^{24}$: N$^{21'}$, $_κ$N$^{22'}$, $_κ$N$^{23'}$, $_κ$N$^{24'}$}}-dizinc Comparative Example 2

Circular dichroism spectra of a sample solution containing 1-phenylethylamine were measured in the same manner as in Example 3 except that the zinc porphyrin dimer (approximately $10^{-6}$ mol/l) used in Comparative Example 1 was used instead of Compound 1 as a reagent for determining the absolute configuration of a chiral compound.

The result is shown by the dotted line in FIG. 6. The absolute configuration of 1-phenylethylamine was not determined since the Cotton effect was not detected. However, the Cotton effect was detected by adjusting the concentration of 1-phenylethylamine to $1\times10^{-3}$ mol/l.

INDUSTRIAL APPLICABILITY

With respect to chiral compounds which can be coordinated to a metalloporphyrin dimer, the present invention allows direct determination of the absolute configuration of an asymmetric carbon atom which is directly bonded to a group capable of coordinating to the metalloporphyrin dimer, or an asymmetric carbon atom separated by one carbon atom from the coordinating group. In the case of a compound having two or more asymmetric carbons, such as menthol, the absolute configuration of the asymmetric carbon to which a group coordinating to a metalloporphyrin dimer is bonded or an asymmetric carbon having one carbon atom separating it from the coordinating group can be determined.

According to the present invention, the absolute configuration of a chiral compound can be determined without complicated processes such as cooling the sample solution.

The present invention provides an extremely sensitive method, and thus trace amounts of chiral compounds are enough for determination of absolute configuration. The amount of metalloporphyrin dimer required is also very small. When an acyclic primary monoamine is taken as an example, the method disclosed in Japanese Unexamined Patent Publication No. 2001-220392 requires at least $10^{-3}$ mol/l of amine for the determination of the absolute configuration, while according to the method of the invention, at least $10^{-6}$ mol/l of amine is enough.

The invention eliminates the necessity of introducing any specific modified groups into the chiral compound for measurement. Therefore, chiral compounds can be easily recovered as required. For example, a complex composed of the metalloporphyrin dimer and a chiral compound decomposes into the free base porphyrin dimer and the hydrochloride of the chiral amine by stirring the sample solution after measurement and about 2 mol/l of aqueous hydrochloric acid solution, thus allowing recovery of the chiral compound by separation. The free base porphyrin dimer recovered by separation can be recycled by introducing an alkaline-earth metal ion again thereinto.

According to the present invention, the absolute configuration of a chiral compound can be determined quite rapidly. The period required for preparing a sample and measuring its CD spectra is less than 10 minutes under a certain condition.

The detection of Cotton effects, i.e., the measurement of CD spectra, is usually carried out in the region from 400 to 450 nm. Most chiral compounds have absorptions up to 400 nm, and thus the peak which shows the Cotton effect and the peaks shown by the chiral compounds themselves do not overlap. Therefore, the invention allows the determination of the absolute configuration of a very wide variety of chiral compounds.

Furthermore, the absolute configuration of non-crystalline compounds can be determined by the present invention.

The invention claimed is:

1. A reagent for determining the absolute configuration of a chiral compound, the reagent containing as an active ingredient a metalloporphyrin dimer comprising two porphyrin rings, wherein the metalloporphyrin dimer has $Mg^{2+}$ as a central metal and has a carbon chain-crosslinked structure in which at least one of the two porphyrin rings has a substituent bulkier than methyl at at least one carbon atom located two carbon atoms away from a carbon atom bonded to the crosslinking carbon chain along the outer periphery of the porphyrin ring, and wherein an induced Cotton effect can be detected by said metalloporphyrin dimer in the case of a chiral compound of a monoalcohol without cooling to about −80° C.

2. A reagent for determining the absolute configuration of a chiral compound according to claim 1, wherein the carbon chain-crosslinked metalloporphyrin dimer is a metalloporphyrin represented by formula (1):

wherein $M^{2+}$ and $M'^{2+}$ are $Mg^{2+}$, n is 2 or 3, $R^a$ to $R^d$ are the same or different and each represent a hydrogen atom or a substituent bulkier than methyl, at least one of $R^a$ to $R^d$ represents a substituent bulkier than methyl, and $R^1$ to $R^{12}$ are the same or different and each represent a hydrogen atom or a hydrocarbon group.

3. A reagent according to claim 2, wherein at least one of $R^a$ to $R^d$ in formula (1) is one member selected from the group consisting of 1) a $C_1$-$C_8$ hydrocarbon group, 2) an oxygen-containing substituent, 3) a nitrogen-containing substituent, 4) a halogen atom, and 5) a halogenated hydrocarbon group.

4. A method for determining the absolute configuration of a chiral compound comprising analyzing a sample solution containing a reagent according to claim 1 and the chiral compound by circular dichroism spectrophotometry to determine the absolute configuration of an asymmetric carbon of the chiral compound based on a sign of the Cotton effect, the chiral compound having the following characteristics:

(i) being capable of coordinating to the metalloporphyrin dimer as an active ingredient, and (ii) having a group capable of coordinating to the metalloporphyrin dimer directly bonded to the asymmetric carbon atom, or having one carbon atom separating the group capable of coordinating to the metalloporphyrin dimer and the asymmetric carbon atom, wherein an induced Cotton effect can be detected by said metalloporphyrin dimer in the case of a chiral compound of a monoalcohol without cooling to about −80° C.

5. A method according to claim 4, wherein the chiral compound is selected from one member of the group consisting of 1) a primary monoamine, 2) a secondary monoamine, 3) a monoalcohol, and 4) an aminoalcohol.

6. A method according to claim 4, wherein the circular dichroism spectrophotometric measurement is conducted at −10° C. to 30° C.

7. A method for determining an absolute configuration of a chiral compound, comprising:

providing a chiral compound (i) being capable of coordinating to the metalloporphyrin dimer according to claim 1 as an active ingredient and (ii) having a group capable of coordinating to the metalloporphyrin dimer directly bonded to an asymmetric carbon atom, or having one carbon atom separating the group capable of coordinating to the metalloporphyrin dimer and the asymmetric carbon atom;

providing a sample solution containing the chiral compound and a reagent, said reagent containing as an active ingredient a metalloporphyrin dimer, wherein the metalloporphyrin dimer has two porphyrin rings and a crosslinking carbon chain which bonds the two porphyrin rings, each porphyrin ring has $Mg^{2+}$ as a central metal, and at least one of the two porphyrin rings has a substituent bulkier than methyl at at least one of carbon atoms which are positioned secondarily along the outer periphery of the porphyrin ring based on a carbon atom bonded to the crosslinking carbon chain; and subjecting the sample solution to circular dichroism spectrophotometry to determine the absolute configuration of an asymmetric carbon of the chiral compound based on a sign of the Cotton effect, wherein an induced Cotton effect can be detected by said metalloporphyrin dimer in the case of a chiral compound of a monoalcohol without cooling to about −80° C.

8. The method according to claim 7, wherein the chiral compound is selected from one member of the group consisting of 1) a primary monoamine, 2) a secondary monoamine, 3) a monoalcohol, and 4) an aminoalcohol.

9. The method according to claim 7, wherein the carbon chain-crosslinked metalloporphyrin dimer is a metalloporphyrin represented by formula (1):

wherein $M^{2+}$ and $M'^{2+}$ are $Mg^{2+}$; n is 2 or 3; $R^a$ to $R^d$ are the same or different and each represent a hydrogen atom or a substituent bulkier than methyl; at least one of $R^a$ to $R^d$ represents a substituent bulkier than methyl; and $R^1$ to $R^{12}$ are the same or different and each represent a hydrogen atom or a hydrocarbon group.

10. The method according to claim 7, wherein the circular dichroism spectrophotometric measurement is conducted at −10° C. to 30° C.

11. A reagent for determining an absolute configuration of a chiral compound, the reagent containing as an active ingredient a metalloporphyrin dimer, wherein the metalloporphyrin dimer has two porphyrin rings and a crosslinking carbon chain which bonds the two porphyrin rings, each porphyrin ring has $Mg^{2+}$ as a central metal, and at least one of the two porphyrin rings has a substituent bulkier than methyl at at least one of carbon atoms which are positioned secondarily along the outer periphery of the porphyrin ring based on a carbon atom bonded to the crosslinking carbon chain, wherein an induced Cotton effect can be detected by said metalloporphyrin dimer in the case of a chiral compound of a monoalcohol without cooling to about −80° C.

12. A mixture of a chiral compound and a reagent for determining an absolute configuration of the chiral compound, said reagent containing as an active ingredient a metalloporphyrin dimer having two porphyrin rings and a crosslinking carbon chain which bonds the two porphyrin rings, each porphyrin ring has $Mg^{2+}$ as a central metal, and at least one of the two porphyrin rings has a substituent bulkier than methyl at at least one of carbon atoms which are positioned secondarily along the outer periphery of the porphyrin ring based on a carbon atom bonded to the crosslinking carbon chain, wherein an induced Cotton effect can be detected by said metalloporphyrin dimer in the case of a chiral compound of a monoalcohol without cooling to about −80° C.

13. The mixture according to claim 12, wherein the carbon chain-crosslinked metalloporphyrin dimer is a metalloporphyrin represented by formula (1):

(1)

wherein $M^{2+}$ and $M'^{2+}$ are $Mg^{2+}$; n is 2 or 3; $R^a$ to $R^d$ are the same or different and each represent a hydrogen atom or a substituent bulkier than methyl; at least one of $R^a$ to $R^d$ represents a substituent bulkier than methyl; and $R^1$ to $R^{12}$ are the same or different and each represent a hydrogen atom or a hydrocarbon group.

14. The mixture according to claim 12, wherein the chiral compound (i) is capable of coordinating to the metalloporphyrin dimer as an active ingredient and (ii) has a group capable of coordinating to the metalloporphyrin dimer directly bonded to an asymmetric carbon atom, or has one carbon atom separating the group capable of coordinating to the metalloporphyrin dimer and the asymmetric carbon atom.

15. The mixture according to claim 14, wherein the chiral compound is selected from one member of the group consisting of 1) a primary monoamine, 2) a secondary monoamine, 3) a monoalcohol, and 4) an aminoalcohol.

16. The mixture according to claim 12, which is a solution.

* * * * *